United States Patent [19]

Hubele et al.

[11] Patent Number: 4,479,004
[45] Date of Patent: Oct. 23, 1984

[54] 1-[2-(4-DIPHENYL)-1,3-DIOXOLAN-2-YL-METHYL]-1-H-TRIAZOLES

[75] Inventors: Adolf Hubele, Magden; Peter Riebli, Basel, both of Switzerland

[73] Assignee: Janssen Pharmaceutica N.V., Beerse, Belgium

[21] Appl. No.: 423,391

[22] Filed: Sep. 24, 1982

Related U.S. Application Data

[63] Continuation of Ser. No. 203,002, Nov. 3, 1980, abandoned.

[51] Int. Cl.$^3$ .................... C07D 405/06; A01N 43/64
[52] U.S. Cl. .................................. 548/101; 424/245; 424/269; 424/273 R; 548/262; 548/336; 548/341
[58] Field of Search ............... 548/101, 262, 336, 341; 424/245, 269, 273 R

[56] References Cited

U.S. PATENT DOCUMENTS

| | | | |
|---|---|---|---|
| 4,073,925 | 2/1978 | Balasubramanyan et al. | 424/273 R |
| 4,079,062 | 3/1978 | Van Reet et al. | 424/269 X |
| 4,101,664 | 7/1978 | Heeres | 424/273 R |
| 4,101,665 | 7/1978 | Heeres | 424/273 R |
| 4,101,666 | 7/1978 | Heeres | 424/273 R |
| 4,102,891 | 7/1978 | Timmler et al. | 548/262 |
| 4,139,540 | 2/1979 | Heeres | 260/340.9 R |
| 4,160,838 | 10/1979 | Van Reet et al. | 424/269 |
| 4,259,505 | 3/1981 | Sturm et al. | 548/262 |
| 4,301,166 | 11/1981 | Regel et al. | 424/269 |

FOREIGN PATENT DOCUMENTS

| | | | |
|---|---|---|---|
| 2706670 | 8/1978 | Fed. Rep. of Germany | 424/245 |
| 1464224 | 2/1977 | United Kingdom | 548/262 |
| 2027701 | 2/1980 | United Kingdom | 548/262 |
| 2026486 | 2/1980 | United Kingdom | 548/262 |

Primary Examiner—Donald G. Daus
Assistant Examiner—Diana G. Rivers
Attorney, Agent, or Firm—Geoffrey G. Dellenbaugh

[57] ABSTRACT

A description is given of new compounds of the formula defined herein:

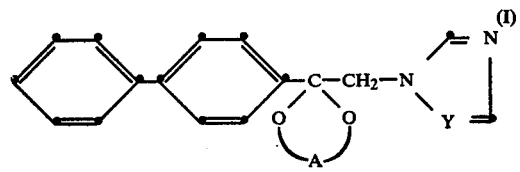

which display valuable microbicidal properties. The compounds can be used for combatting microorganisms harmful to plants, especially phytopathogenic fungi. The compounds of formula I thus possess a curative, systemic, and preventive action very useful for practical requirements for the protection of cultivated plants, without causing these to suffer any undesirable side effects. In practice, the compounds can be used by themselves or in the form of pesticides.

4 Claims, No Drawings

1-[2-(4-DIPHENYL)-1,3-DIOXOLAN-2-YL-METHYL]-1-H-TRIAZOLES

This is a continuation of application Ser. No. 203,002, filed Nov. 3, 1980, now abandoned.

The present invention relates to substituted 1-[2-(4-diphenyl)ethyl]-1H-azolylketals of formula I and their plant-compatible salts with inorganic or organic acids and their metal complexes, to the manufacture of compounds of this type, and moreover to microbicidal agents containing the compounds of formula I as the active principles and to the use of compounds of formula I for combatting plant diseases.

The invention comprises compounds of formula I

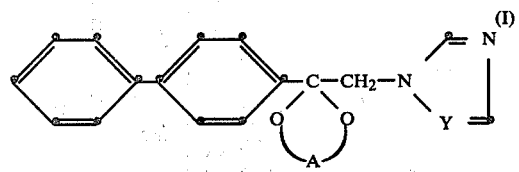

in which Y represents CH or N and A represents one of the following alkylene bridges

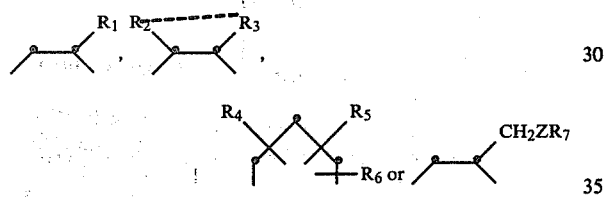

where Z stands for oxygen or sulfur, $R_1$ for hydrogen or possibly a halogen-substituted $C_1$–$C_4$ alkyl, $R_2$ represents methyl or ethyl, $R_3$ represents methyl, ethyl, or propyl, or $R_2$ and $R_3$ together form a tetramethylene bridge, and $R_4$, $R_5$, and $R_6$ represent independently of one another hydrogen or $C_1$–$C_4$ alkyl, the total number of carbon atoms in $R_4$, $R_5$, and $R_6$ not exceeding 6, and $R_7$ represents hydrogen or possibly $C_1$–$C_2$-alkoxy-substituted $C_1$–$C_6$ alkyl and in addition $C_3$–$C_4$ alkenyl, 2-propinyl, 3-halo-2-propinyl, or possibly a halogen-, alkyl-, alkoxy-, nitro- or trifluoromethyl-substituted phenyl or substituted benzyl, with the inclusion of their plant-compatible acid addition salts with organic and inorganic acids and their metal complex salts.

Depending on the number of the carbon atoms given, by alkyl or alkyl fraction the following groups, for example, are meant: methyl, ethyl, propyl, butyl, pentyl, or hexyl and their isomers such as isopropyl, isobutyl, tert.butyl, isopentyl, etc. Alkenyl stands for propenyl-(1), allyl, butenyl-(1), butenyl-(2), and butenyl-(3). Here and in what follows the term halogen represents fluorine, chlorine, bromine, or iodine, and preferably chlorine or bromine.

Examples of inorganic acids are hydrochloric acid, hydrobromic acid, hydroiodic acid, sulfuric acid, phosphoric acid, phosphorous acid, and nitric acid.

Examples of organic acids are acetic acid, trichloroacetic acid, oxalic acid, benzenesulfonic acid, and methanesulfonic acid.

The metal complexes of formula I consist of the basic organic molecule and an inorganic or organic metal salt, such as the halide, nitrate, sulfate, phosphate, tartrate, etc. of copper, manganese, iron, zinc, and other metals. The metal cations can be present in the various valences appropriate to them.

The compounds of formula I exhibit a very useful microbicidal spectrum. They can be used, for example, against phytopathogenic microorganisms, in particular against fungi that are harmful to plants. The 1,2,4-triazolyl derivatives encompassed by formula I are preferred.

The compounds of formula I, with the inclusion of their salts and metal complexes, in which Y represents nitrogen and Z represents oxygen, $R_1$ stands for $C_1$–$C_4$ alkyl, $R_2$ for methyl or ethyl, $R_3$ for methyl or ethyl, $R_4$, $R_5$, and $R_6$ represent independently of one another hydrogen or a methyl group, and $R_7$ stands for hydrogen, methyl, or ethyl (this group shall be known as Ia) constitute a preferred group of microbicides. Particularly preferred are the copper salt complexes of this group Ia.

The compounds of formula I, with the inclusion of their salts and metal complexes, in which Y stands for —CH and Z stands for oxygen, $R_1$ stands for $C_1$–$C_4$ alkyl, $R_2$ for methyl or ethyl, $R_3$ for methyl or ethyl, $R_4$, $R_5$, and $R_6$ represent independently of one another hydrogen or a methyl group, and $R_7$ stands for hydrogen, methyl, or ethyl (this group shall be referred to as Ib) constitute a further group of microbicides.

In addition, the following individual compounds are particularly preferred:

1-[2-(4-diphenyl)-4,5-dimethyl-1,3-dioxolan-2-yl-methyl]-1H-1,2,4-triazole, including its acid addition salts and metal complexes, especially in view of its strong action against Alternaria. Copper complexes of this compound are particularly preferred, e.g., compound no. 2.24 which is named hereinafter.

1-[2-(4-diphenyl)-4-methyl-1,3-dioxolan-2-yl-methyl]-1H-1,2,4-triazole, including its acid addition salts and metal complexes.

The following imidazole compounds are also of interest:

1-[2-(4-diphenyl)-4,5-dimethyl-1,3-dioxolan-2-yl-methyl]-1H-imidazole, including its acid addition salts and metal complexes.

1-[2-(4-diphenyl)-4-ethyl-1,3-dioxolan-2-yl-methyl]-1H-imidazole, including its acid addition salts and metal complexes.

The compounds of formula I can be manufactured by a whole series of reaction variants, such as are outlined below in a reaction scheme and which are listed in detail below. In formulas II to XIII $R_7$, A, Y, and Z have the meanings stated in formula I. Me stands for hydrogen or preferably a metal atom and in particular an alkali metal atom. X represents one of the usual leaving groups such as a halogen, in particular chlorine, bromine, or iodine or benzenesulfonyl, p-tosyl, trifluoroacetyl, or preferably a lower alkylsulfonyl group such as mesyl. Ar stands for

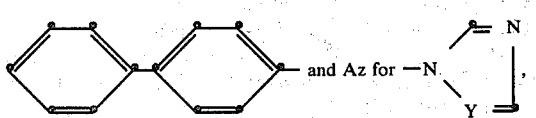

Y representing —CH= or =N=.

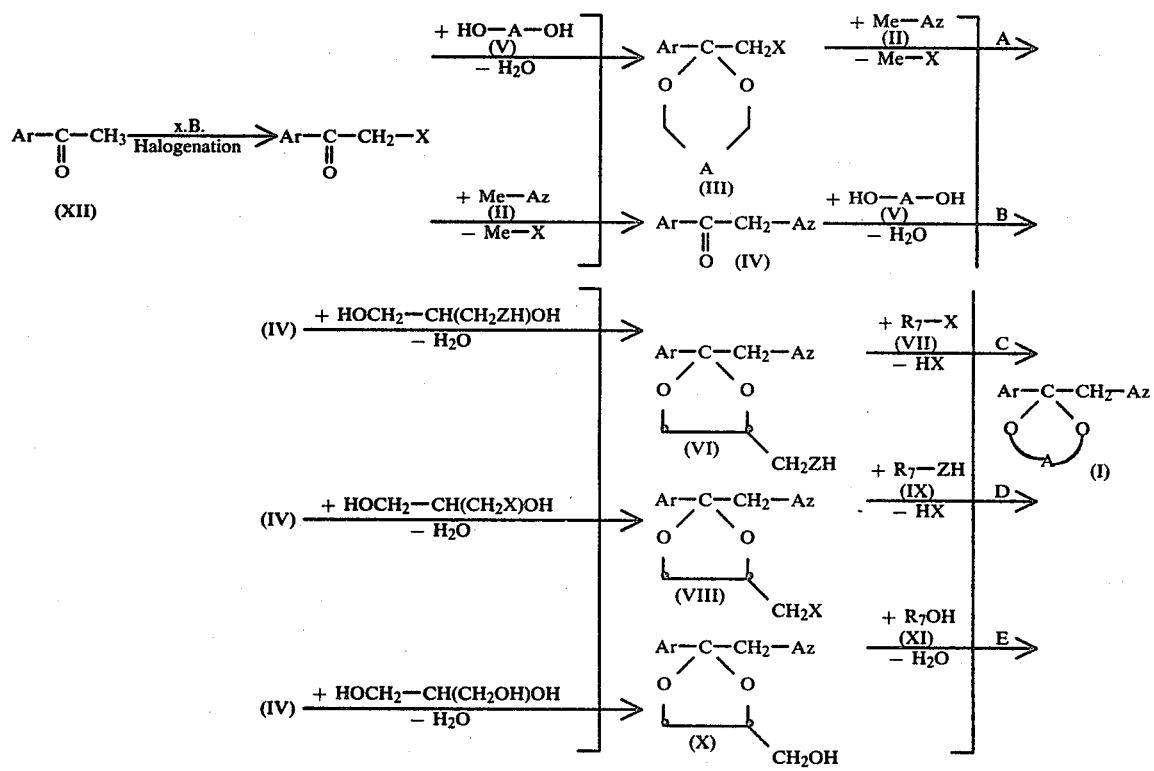

Specifically, it is possible to proceed as follows:

A. Ketals of formula I can be manufactured by reacting an azole of formula II:

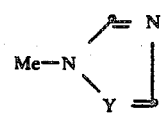

(II)

where Y stands for —CH= or —N= and Me stands for hydrogen or preferably a metal atom, and particularly an alkali metal atom, with a compound of formula III:

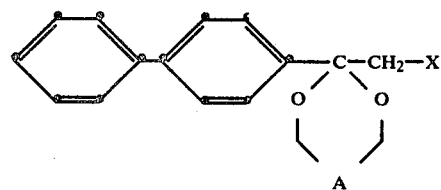

(III)

where A has the same meaning as under formula I and X represents one of the usual leaving groups, for example a halogen, especially chlorine, bromine, or iodine, or benzenesulfonyl, p-tosyl, trifluoroacetyl, or preferably a low alkylsulfonyl group such as mesyl.

The reaction of II with III is preferably performed in a relatively polar but reaction-inert organic solvent such as N,N-dimethylformamide, N,N-dimethylacetamide, dimethyl sulfoxide, acetonitrile, benzonitrile, etc. Solvents of this kind can be used in combination with other reaction-inert solvents, such as aliphatic or aromatic hydrocarbons, for example benzene, toluene, xylene, hexane, petroleum ether, chlorobenzene, nitrobenzene, and so on.

If X represents chlorine or bromine it is expedient to use an alkali metal iodide (such as NaI or KI) to accelerate the reaction. Elevated temperatures of 0° to 220° C., and preferably 80° to 170° C., are advantageous. It is expedient for the reaction mixture to be heated under reflux.

If, in formula II, Me stands for hydrogen, the process is performed in the presence of a base. Examples of such bases are inorganic bases such as the oxides, hydroxides, hydrides, carbonates, and hydrogen carbonates of alkali metals and alkaline earth metals, and also for example tertiary amines like triethylamine, triethylenediamine, piperidine, pyridine, 4-dimethylaminopyridine, 4-pyrrolidylpyridine, etc.

In the case of these and the following preparation variants the intermediate products and the end products can be isolated from the reaction medium and, if desired, be purified using one of the methods in general use, e.g. by extraction, crystallization, chromatography, distillation, etc.

B. Another variant for the manufacture of the compounds of formula I consists in a ketalization reaction of a ketone of formula IV:

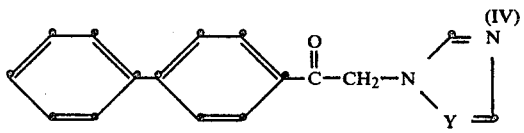

(IV)

in which Y stands for —CH= or —N=, in the presence of an acid, with a diol of formula V:

 (V)

where A has the same meaning as given in formula I.

This ketalization reaction can be performed analogously to ketalizations already known, for example in the same way as the manufacture of 2-bromomethyl-2,4-diphenyl-1,3-dioxolane [Synthesis, 1974, (I), 23].

In the preferred embodiment of the ketalization the two reaction partners are refluxed for several hours together with an azeotrope-former in one of the customary organic solvents. Suitable azeotrope-formers are, for example, benzene, toluene, xylene, chloroform, or carbon tetrachloride. In this case the reaction is performed, for example, in the presence of a simple alcohol such as ethanol, propanol, butanol, pentanol, etc., an addition of a strong acid such as p-toluenesulfonic acid being sometimes advantageous to accelerate the reaction. Organic solvents that can be used in this case are, for example, aromatic hydrocarbons such as benzene, toluene, xylene, etc. and saturated hydrocarbons such as n-hexane.

Other methods of ketalization are also possible, such as ketalization of the ketone IV with another diol or alkanol and then trans-ketalization of the ring-ketal or open ketal thus obtained to I by reaction with an excess of the diol V.

C. Especially when in compounds of formula I the substituent A stands for —CH$_2$—CH(CH$_2$ZR$_7$)—, the latter can be prepared by reaction of a compound of formula VI:

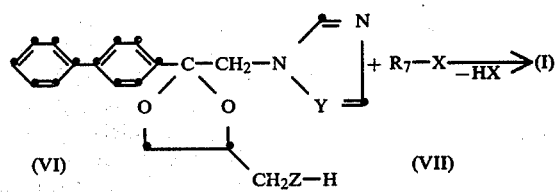

(VI)

with a reactive compound of formula VII suitable for O-alkylation or S-alkylation, where Y, Z, and R$_7$ have the meanings given under formula I and X has the meaning given in variant A.

The reaction is preferably performed in reaction-inert organic solvents. Suitable solvents for this purpose are, for example, N,N-dimethylformamide, N,N-dimethylacetamide, hexamethylphosphorus triamide, dimethyl sulfoxide, 4-methyl-2-pentanone, etc. It is also possible to use mixtures with other reaction-inert solvents, for example with aromatic hydrocarbons like benzene, toluene, xylene, etc. In many cases it can prove advantageous to accelerate the reaction rate by working in the presence of a base. Suitable bases of this type are, for example, alkali metal hydrides or alkali metal carbonates. In certain cases it can also be beneficial first to convert the compound VI in a known manner into a suitable metal salt. This is preferably done by reacting VI with an Na compound such as sodium hydride, sodium hydroxide, etc. This salt of VI is thereafter reacted with the compound of formula VII. To accelerate the reaction rate it is possible in many cases to work at an elevated temperature, preferably 80° to 130° C., or at the boiling point of the solvent.

D. For the manufacture of the compounds of formula I, in which A stands for —CH$_2$—CH(CH$_2$ZR$_7$)—, a ketal of formula VIII:

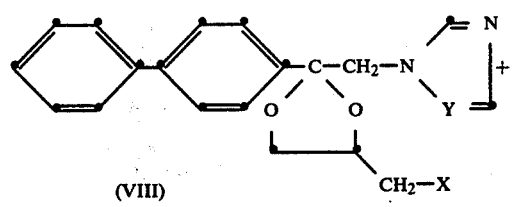

(VIII)

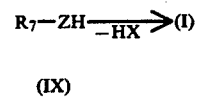

(IX)

can also be allowed to react with a compound of formula IX; in this case R$_7$, X, Y, and Z have the meanings described under variant C.

E. If Z in the products of formula I represents oxygen, these products can also be obtained by condensation of an alcohol of formula X with an alkanol of formula XI.

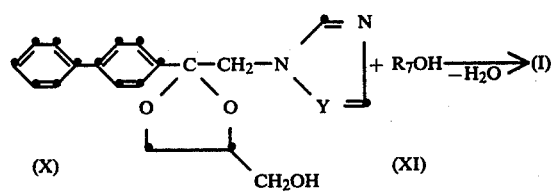

(X) (XI)

In this case R$_7$ and Y have the same meanings as in formula I.

In this condensation the reactants can be heated in a suitable solvent under reflux, the water azeotrope produced being simultaneously distilled off from the reaction mixture. Suitable solvents are aromatic hydrocarbons such as n-hexane or the alcohol XI itself. In this reaction it is expedient to work in the presence of a strong acid such as p-toluenesulfonic acid.

If the compounds of formula I are obtained as bases they can be converted into corresponding salts by inorganic or organic acids or into metal complexes of formula I by preferably equimolar amounts of metal salts. Conversely, salts of formula I can be converted into the free bases of formula I, for example by reacting them with an alkali metal (hydrogen) carbonate or alkali metal hydroxide.

The starting ketals of formula III can be obtained from the basic 4-acetylbiphenyl of formula XII:

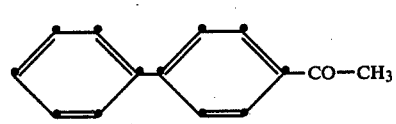

(XII)

by reaction with the desired diol in an inert solvent, e.g. a halogenated hydrocarbon (such as methylene chloride, ethylene chloride, chloroform, carbon tetrachloride, etc.) and by simultaneous or subsequent halogenation. To accelerate the reaction it is advantageous to add p-toluenesulfonic acid.

The ketones of formula IV can be manufactured by halogenation of the starting ketones XII to XIII:

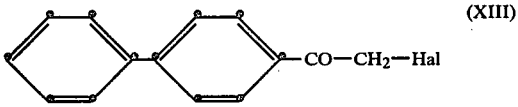 (XIII)

d by further reacting XIII in the same way as in variant A with an azole of formula II. In this case Hal is eferably chlorine or bromine.

The ketals VI, VIII, and X are obtained in the same ay as in variant B by reacting the starting ketone IV ith a suitable α,β-diol.

The preparation variants described are an essential omponent of the invention.

In all the described ketalizations of a ketone with a bstituted α,β-diol mixtures of diastereomers of the sultant ketal can be produced. Correspondingly, diasreomeric end products of formula I are then formed om the starting ketones. The individual isomers exbit different microbicidal actions. The invention retes to all the isomeric compounds, to their salts, and to eir metal complexes.

The manufacturing processes of compounds of forula I in its described variants A, B, C, D, and E is an sential component of the invention.

Some of the starting substances and intermediate oducts used in processes A, B, C, D, and E are familr, and others can be prepared by methods known in emselves. Some are new; their preparation is deribed here.

1-(β-Aryl)-ethylimidazolylketals, in which the aryl ands for substituted phenyl or naphthyl are cited in the llowing references as fungicides and bactericides: .S. Pat. Nos. 3,575,999; 3,936,470; 4,101,664; 101,666; and 4,156,008.

Surprisingly, it has been found that compounds of rmula I display a microbicidal spectrum very favorle for practical requirements. For example, they can used to protect cultivated plants.

The main field of application of compounds of forula I lies in combatting harmful microorganisms, ove all phytopathogenic fungi. Accordingly, the mpounds of formula I possess a curative, preventive, d systemic action for the protection of cultivated ants that is very favorable for practical requirements d that does not have any side effects on the plants.

he cultivated plants within the scope of the present vention are, for example: cereal crops (wheat, barley, 'e, oats, rice), beets (sugar beet and fodder beet), pip d stone fruits and small fruits (apples, pears, plums, aches, almonds, cherries, strawberries, raspberries, d blackberries), leguminous plants (beans, lentils, as, soya beans), oil cultures (rape, mustard, poppy, ives, sunflowers, coconuts, castor-oil plants, cocoa, anuts), cucumber-like plants (pumpkins, cucumbers, elons), fibrous plants (cotton, flax, hemp, jute), citrus uits (oranges, lemons, grapefruits, tangerines), vegetaes (spinach, cabbage lettuce, asparagus, cabbages, rrots, onions, tomatoes, potatoes, paprika), or plants ich as maize, tobacco, nuts, coffee, sugar cane, tea, rapevines, hops, bananas, and natural rubber plants d ornamental plants.

By using the active principles of formula I the microrganisms occurring on plants or parts of plants (fruit, lossom, foliage, stem, tuber, roots) of these and relates seful cultures can be checked or destroyed, the subseuently growing parts of the plants being unaffected by ich microorganisms. The active principles are effective against the phytopathogenic fungi belonging to the following classes: Ascomycetes (e.g. Venturia, Podosphaera, Erysiphaceae, Fusarium, Helminthosporium), Basidiomycetes such as above all rust fungi (e.g. Puccinia), fungi imperfecti (e.g. Moniliales etc., Botrytis, and the Cercospora and Alternaria pathogens belonging to the family of Dematiaceae and the Oomycetes belonging to the Phycomycetes, such as Plasmopara. Moreover, the compounds of formula I exert a systemic action. They can also be used as disinfectants for the treatment of seed (fruits, tubers, grain) and of plant cuttings for protection against fungal infections and against phytopathogenic fungi occurring in the soil.

The invention thus relates in addition to the use of the compounds of formula I for combatting phytopathogenic microorganisms and for the preventive inhibition of plant disease.

To combat these microorganisms the compounds of formula I can be used by themselves or together with suitable carriers and/or other additions. Suitable carriers and additives can be solid or liquid and correspond to the substances usual in formulation technology, such as natural or regenerated inorganic substances, solvents, dispersing agents, cross-linking agents, adhesives, thickeners, bonding agents, or fertilizers. The active principles of formula I can also be used in mixtures, for example with pesticidal or plant-growth promoting preparations.

The following examples are intended to illustrate more closely the nature of agents of this kind.

The contents of the active principle in the commercial preparations is between 0.0001 and 90%.

The 1-(β-diphenyl)ethylazolylketals of formula I in accordance with the invention exhibit, in comparison with the cited compounds, a better microbicidal spectrum for the protection of cultivated plants and are characterized by the absence of phytotoxicity while entailing the dosages usual in plant protection, so that they protect cultivated plants from harmful microorganisms without damaging them in the process.

In the following examples the temperatures are given in degrees Celsius and the parts refer to parts by weight.

EXAMPLE 1

Preparation of

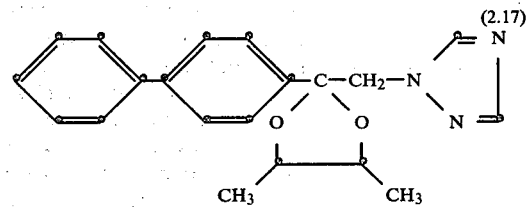 (2.17)

1-[2-(4-diphenyl)-4,5-dimethyl-1,3-dioxolan-2-ylmethyl]-1H-1,2,4-triazole 13.8 parts of 1,2,4-triazole, 27.6 parts of potassium carbonate, and a catalytically active quantity of sodium iodide are mixed in 70 ml of dimethyl sulfoxide and treated to a dropwise addition of 64.2 parts of 2-(4-diphenyl)-2-bromomethyl-4,5-dimethyldioxolane(1,3) in 50 ml of dimethyl sulfoxide, after which the reaction mixture is stirred for 48 h at an internal temperature of 130° C. After cooling to room temperature, 250 ml of water are added and the crude product precipitated is filtered off and recrystallized from isopropanol. The beige-colored crystals melt at 125°–133° C.

The following end products of formula I are prepared in a similar manner:

TABLE 1

Compounds of formula I with A = , including isomeric forms:

| Compound No. | $R_1$ | Y | Salt | Physical constants |
|---|---|---|---|---|
| 1.1 | H | N | — | m.p. 129–132° |
| 1.2 | H | N | $HNO_3$ | |
| 1.3 | H | CH | — | |
| 1.4 | $CH_3$ | N | — | m.p. 103–105° |
| 1.5 | $CH_3$ | N | $HNO_3$ | m.p. 131–133° |
| 1.6 | $CH_3$ | N | $CuCl_2$ | |
| 1.7 | $CH_3$ | CH | — | |
| 1.8 | $CH_3$ | N | $Mn(NO_3)_2$ | |
| 1.9 | $C_2H_5$ | N | — | m.p. 93–115° |
| 1.10 | $C_2H_5$ | N | $HNO_3$ | m.p. 126–127° |
| 1.11 | $C_2H_5$ | N | $ZnCl_2$ | |
| 1.12 | $C_2H_5$ | N | $Mn(NO_3)_2$ | |
| 1.13 | $C_2H_5$ | N | $FeCl_3$ | |
| 1.14 | $C_2H_5$ | CH | — | m.p. 109–117° |
| 1.15 | $C_2H_5$ | CH | $CuCl_2$ | |
| 1.16 | $C_3H_7-n$ | CH | — | |
| 1.17 | $C_3H_7-n$ | N | — | m.p. 66–73° |
| 1.18 | $C_3H_7-n$ | N | $ZnCl_2$ | |
| 1.19 | $C_3H_7-n$ | N | $HNO_3$ | m.p. 141–144° (dec) |
| 1.20 | $C_4H_9-n$ | N | — | |
| 1.21 | $C_4H_9-n$ | CH | — | |
| 1.22 | $CH_2Cl$ | N | — | |

TABLE 2

Compounds of formula I with A = , including isomeric forms

| Compound No. | $R_2$ | $R_3$ | Y | Salt | Physical constants |
|---|---|---|---|---|---|
| 2.1 | $CH_3$ | $C_2H_5$ | CH | — | |
| 2.2 | $CH_3$ | $C_2H_5$ | N | — | m.p. 52–68° |
| 2.3 | $CH_3$ | $C_2H_5$ | CH | $HNO_3$ | |
| 2.4 | $CH_3$ | $C_2H_5$ | N | $HNO_3$ | m.p. 86–88° |
| 2.5 | $CH_3$ | $C_3H_7-n$ | CH | — | |
| 2.6 | $CH_3$ | $C_3H_7-n$ | N | — | |
| 2.7 | $CH_3$ | $C_3H_7-n$ | N | $HNO_3$ | |
| 2.8 | $CH_3$ | $C_3H_7-n$ | N | $Mn(NO_3)_2$ | |
| 2.9 | $CH_3$ | $CH_3$ | CH | — | m.p. 74–78° |
| 2.10 | $CH_3$ | $CH_3$ | CH | $CuCl_2$ | |
| 2.11 | $CH_3$ | $C_2H_5$ | CH | $Mn(NO_3)_2$ | |
| 2.12 | $CH_3$ | $C_2H_5$ | CH | $CuCl_2$ | |
| 2.13 | $CH_3$ | $C_2H_5$ | N | $CuCl_2$ | m.p. 138–142° |
| 2.14 | $CH_3$ | $C_2H_5$ | N | $ZnCl_2$ | |
| 2.15 | $CH_3$ | $C_2H_5$ | N | $Mn(NO_3)_2$ | |
| 2.16 | $CH_3$ | $C_2H_5$ | N | $FeCl_3$ | |
| 2.17 | $CH_3$ | $CH_3$ | N | — | m.p. 125–133° |
| 2.18 | $CH_3$ | $CH_3$ | N | $HNO_3$ | m.p. 153–154°(dec) |
| 2.19 | $C_2H_5$ | $CH_3$ | CH | $MnCl_2$ | |
| 2.20 | $C_2H_5$ | $CH_3$ | N | $MnCl_2$ | |
| 2.21 | $C_2H_5$ | $CH_3$ | N | $CuCl_2$ | |
| 2.22 | $C_2H_5$ | $CH_3$ | N | $ZnCl_2$ | |
| 2.23 | $C_2H_5$ | $C_2H_5$ | CH | — | |
| 2.24 | $CH_3$ | $CH_3$ | N | $CuCl_2$ | m.p. 208–212° |
| 2.25 | $C_2H_5$ | $C_2H_5$ | N | — | |
| 2.26 | $C_2H_5$ | $C_2H_5$ | N | $HNO_3$ | |
| 2.27 | $CH_3$ | $CH_3$ | N | $ZnCl_2$ | m.p. 191–192° |
| 2.28 | $C_2H_5$ | $C_3H_7-n$ | N | — | |
| 2.29 | $C_2H_5$ | $C_3H_7-i$ | N | — | |
| 2.30 | $C_2H_5$ | $C_3H_7-n$ | CH | — | |
| 2.31 | $C_2H_5$ | $C_3H_7-n$ | N | HCl | |
| 2.32 | $C_2H_5$ | $C_2H_5$ | N | $Mn(NO_3)_2$ | |
| 2.33 | $CH_3$ | $C_2H_5$ | N | $(COOH)_2$ | |
| 2.34 | $CH_3$ | $C_2H_5$ | CH | $(COOH)_2$ | |
| 2.35 | $CH_3$ | $C_3H_7-i$ | N | — | |
| 2.36 | $CH_3$ | $C_3H_7-i$ | N | $H_2SO_4$ | |
| 2.37 | $-(CH_2)_4-$ | | CH | — | |
| 2.38 | $-(CH_2)_4-$ | | CH | $HNO_3$ | |
| 2.39 | $-(CH_2)_4-$ | | N | — | m.p. 121–122° |
| 2.40 | $-(CH_2)_4-$ | | N | $HNO_3$ | m.p. 171–172° |
| 2.41 | $-(CH_2)_4-$ | | N | $CuCl_2$ | m.p. 217–222° |
| 2.42 | $-(CH_2)_4-$ | | N | $ZnCl_2$ | m.p. 178–184° |
| 2.43 | $-(CH_2)_4-$ | | N | HCl | |
| 2.44 | $-(CH_2)_4-$ | | CH | $ZnCl_2$ | |

TABLE 3

Compounds of the formula

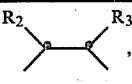

, (XIV)

including isomeric forms

| Compound No. | $R_8$ | $R_9$ | $R_{10}$ | Y | Salt | Physical constants |
|---|---|---|---|---|---|---|
| 3.1 | H | $CH_3$ | H | N | — | |
| 3.2 | H | $C_2H_5$ | H | N | — | |
| 3.3 | H | $CH_3$ | H | CH | — | |
| 3.4 | $CH_3$ | $CH_3$ | H | N | — | |
| 3.5 | $CH_3$ | $CH_3$ | H | N | $HNO_3$ | |
| 3.6 | $CH_3$ | $CH_3$ | $CH_3$ | N | — | |
| 3.7 | $CH_3$ | $CH_3$ | $CH_3$ | N | $HNO_3$ | |
| 3.8 | $CH_3$ | $CH_3$ | $CH_3$ | N | $ZnCl_2$ | |
| 3.9 | $CH_3$ | $CH_3$ | $CH_3$ | N | $Mn(NO_3)_2$ | |
| 3.10 | $CH_3$ | $CH_3$ | $CH_3$ | N | $CuCl_2$ | |
| 3.11 | $CH_3$ | $CH_3$ | $CH_3$ | N | $(COOH)_2$ | |
| 3.12 | $CH_3$ | $CH_3$ | $CH_3$ | CH | $HNO_3$ | |

TABLE 3-continued

Compounds of the formula

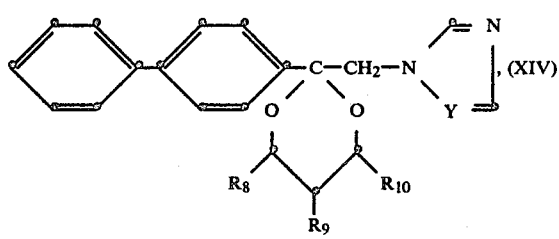

including isomeric forms

| Compound No. | $R_8$ | $R_9$ | $R_{10}$ | Y | Salt | Physical constants |
|---|---|---|---|---|---|---|
| 3.13 | $CH_3$ | $CH_3$ | $CH_3$ | CH | $CuCl_2$ | |
| 3.14 | $CH_3$ | $CH_3$ | $CH_3$ | CH | $FeCl_3$ | |
| 3.15 | $CH_3$ | H | $CH_3$ | N | — | |
| 3.16 | $CH_3$ | H | $C_2H_5$ | N | — | |
| 3.17 | $C_2H_5$ | H | $C_2H_5$ | N | — | |
| 3.18 | $CH_3$ | H | H | N | — | m.p. 117–121° |
| 3.19 | $CH_3$ | H | H | N | $CuCl_2$ | m.p. 211.5–214.5° |
| 3.20 | $CH_3$ | $C_2H_5$ | H | N | — | |
| 3.21 | $CH_3$ | $C_2H_5$ | H | CH | — | |
| 3.22 | $C_2H_5$ | $C_2H_5$ | $CH_3$ | N | — | |
| 3.23 | $C_2H_5$ | $C_2H_5$ | $C_2H_5$ | N | $Mn(NO_3)_2$ | |
| 3.24 | $C_3H_7$-n | H | $C_3H_7$-n | N | — | |
| 3.25 | $C_3H_7$-n | H | $C_3H_7$-n | CH | — | |
| 3.26 | $C_3H_7$-n | $C_3H_7$-n | H | N | — | |
| 3.27 | $C_3H_7$-n | $C_2H_5$ | $CH_3$ | N | — | |
| 3.28 | $C_3H_7$-n | $C_2H_5$ | $CH_3$ | CH | — | |
| 3.29 | $C_3H_7$-n | $C_2H_5$ | $CH_3$ | N | $ZnCl_2$ | |
| 3.30 | $C_3H_7$-n | $CH_3$ | $C_2H_5$ | N | — | |
| 3.31 | $C_2H_5$ | $C_3H_7$-n | $CH_3$ | N | — | |
| 3.32 | $C_4H_9$-n | $CH_3$ | H | N | — | |
| 3.33 | $C_4H_9$-n | H | $CH_3$ | N | $FeCl_3$ | |
| 3.34 | $C_4H_9$-n | H | $CH_3$ | CH | — | |
| 3.35 | $CH_3$ | H | $C_4H_9$-n | N | — | |
| 3.36 | H | H | $C_4H_9$-n | N | — | |
| 3.37 | H | H | $C_4H_9$-n | CH | — | |
| 3.38 | H | H | $C_4H_9$-n | N | $HNO_3$ | |
| 3.39 | H | $C_4H_9$-n | H | N | — | |
| 3.40 | H | $C_4H_9$-n | $CH_3$ | CH | HCl | |
| 3.41 | $CH_3$ | $C_4H_9$-n | H | N | — | |
| 3.42 | H | $C_4H_9$-sek | H | N | $HNO_3$ | |
| 3.43 | H | $C_4H_9$-sek | H | N | — | |
| 3.44 | H | $C_4H_9$-sek | $CH_3$ | N | — | |
| 3.45 | H | $C_4H_9$-sek | $CH_3$ | CH | — | |
| 3.46 | H | $C_3H_7$-i | $CH_3$ | N | — | |
| 3.47 | H | $C_3H_7$-i | $CH_3$ | N | $Mn(NO_3)_2$ | |
| 3.48 | $CH_3$ | $C_3H_7$-i | $CH_3$ | N | — | |
| 3.49 | $C_2H_5$ | $C_3H_7$-i | H | N | — | |

TABLE 4

Compounds of the formula

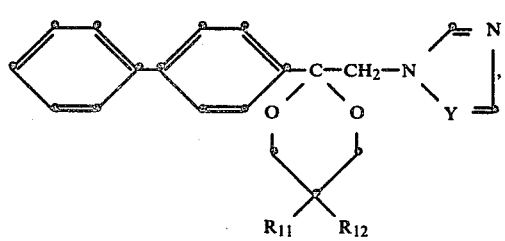
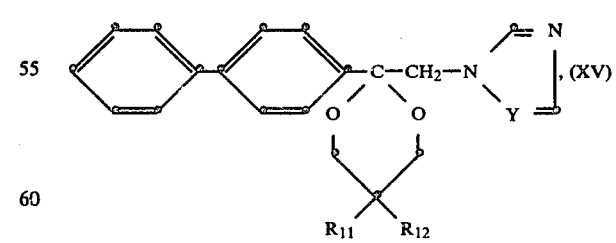

including isomeric forms

| Compound No. | $R_{11}$ | $R_{12}$ | Y | Salt | Physical constants |
|---|---|---|---|---|---|
| 4.1 | H | $CH_3$ | N | — | |
| 4.2 | H | $CH_3$ | CH | — | |
| 4.3 | $CH_3$ | $CH_3$ | N | — | m.p. 96–100° |
| 4.4 | $CH_3$ | $CH_3$ | N | $HNO_3$ | m.p. 132–134° |
| 4.5 | $CH_3$ | $CH_3$ | N | $Mn(NO_3)_2$ | |
| 4.6 | $CH_3$ | $CH_3$ | CH | — | m.p. 132–140° |

TABLE 4-continued

Compounds of the formula

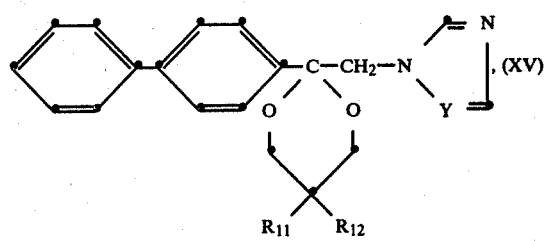

including isomeric forms

| Compound No. | $R_{11}$ | $R_{12}$ | Y | Salt | Physical constants |
|---|---|---|---|---|---|
| 4.7 | $CH_3$ | $CH_3$ | CH | $ZnCl_2$ | |
| 4.8 | $CH_3$ | $C_2H_5$ | N | — | m.p. 132–139° |
| 4.9 | $CH_3$ | $C_2H_5$ | N | $CuCl_2$ | m.p. 203–211° |
| 4.10 | $CH_3$ | $C_2H_5$ | CH | $(COOH)_2$ | |
| 4.11 | $C_2H_5$ | $C_2H_5$ | N | $HNO_3$ | |
| 4.12 | $C_2H_5$ | $C_2H_5$ | N | — | m.p. 106.5–108.5° |
| 4.13 | $C_2H_5$ | $C_2H_5$ | CH | HCl | |
| 4.14 | $C_2H_5$ | $C_2H_5$ | CH | $FeCl_3$ | |
| 4.15 | $C_2H_5$ | $C_2H_5$ | CH | — | m.p. 109–112° |
| 4.16 | H | $C_2H_5$ | N | — | |
| 4.17 | H | $C_2H_5$ | N | $HNO_3$ | |
| 4.18 | H | $C_2H_5$ | CH | — | |
| 4.19 | $CH_3$ | $C_3H_7$-n | N | $CuCl_2$ | m.p. 214–217° |
| 4.20 | H | $C_3H_7$-n | CH | — | |
| 4.21 | $CH_3$ | $C_3H_7$-n | N | $HNO_3$ | m.p. 188–189° (dec) |
| 4.22 | $CH_3$ | $C_3H_7$-n | CH | $(COOH)_2$ | |
| 4.23 | $CH_3$ | $C_3H_7$-n | N | — | m.p. 130.5–133° |
| 4.24 | $CH_3$ | $C_3H_7$-n | CH | — | |
| 4.25 | H | $C_4H_9$-n | N | — | |
| 4.26 | $CH_3$ | $C_4H_9$-n | N | — | |
| 4.27 | $CH_3$ | $C_4H_9$-n | CH | — | |
| 4.28 | $C_2H_5$ | $C_4H_9$-n | N | $HNO_3$ | |

TABLE 5 and the following compounds of the formula

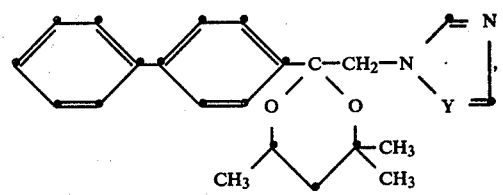

including isomeric forms

| Compound No. | Y | Salt | Physical constants |
|---|---|---|---|
| 5.1 | N | — | m.p. 124–127° |
| 5.2 | CH | — | |
| 5.3 | N | $HNO_3$ | m.p. 161–163° |
| 5.4 | N | $Cl_3CCOOH$ | |
| 5.5 | N | $CuCl_2$ | m.p. 202–210° |
| 5.6 | N | $ZnCl_2$ | |
| 5.7 | N | $Mn(NO_3)_2$ | |
| 5.8 | N | HCl | |
| 5.9 | N | $(COOH)_2$ | |
| 5.10 | CH | $HNO_3$ | |
| 5.11 | CH | $Cl_3CCOOH$ | |
| 5.12 | CH | $CuCl_2$ | |
| 5.13 | CH | $ZnCl_2$ | |
| 5.14 | CH | $Mn(NO_3)_2$ | |
| 5.15 | CH | HCl | |

TABLE 6 as well as the following compounds of formula I with $$A = \text{} CH_2ZR_7$$

including their isomeric forms

| Compound No. | $ZR_7$ | Y | Salt | Physical constants |
|---|---|---|---|---|
| 6.1 | $OCH_3$ | N | — | m.p. 112–114° |
| 6.2 | $OCH_3$ | CH | — | |
| 6.3 | $OCH_3$ | N | $HNO_3$ | m.p. 150–151° |
| 6.4 | $OCH_3$ | N | $CuCl_2$ | m.p. 185–186° |
| 6.5 | $OCH_3$ | N | $Mn(NO_3)_2$ | |
| 6.6 | $OC_2H_5$ | N | — | m.p. 98–102° |
| 6.7 | $OC_2H_5$ | CH | — | |
| 6.8 | $OC_2H_5$ | N | $ZnCl_2$ | |
| 6.9 | $OC_4H_9$-n | N | — | m.p. 65–68° |
| 6.10 | $OC_4H_9$-n | CH | — | |
| 6.11 | $OC_4H_9$-n | N | $CuCl_2$ | m.p. 137–138° |
| 6.12 | $OC_6H_4Cl(4)$ | N | — | m.p. 139–140° |
| 6.13 | $OC_6H_4Cl(4)$ | N | $CuCl_2$ | m.p. 215–216° |
| 6.14 | $SCH_3$ | N | — | |
| 6.15 | $OC_6H_4Cl(4)$ | N | $HNO_3$ | m.p. 166–167° |
| 6.16 | $SC_3H_7$-n | CH | — | |

For application, the compounds of formula I can be used in the following working forms.

FORMULATION EXAMPLES

Solid working forms:

Dusting and scattering materials generally contain up to 100% of the active principle. A 5% dusting agent may, for example, consist of 5 parts of the active principle and 95 parts of an additive such as talc or of 5 parts of active principle, 3 parts of highly dispersed silica, and 92 parts of talc. In addition, further mixtures with carrier materials and additives such as these and others usual in formulation technology are conceivable. In the preparation of these dusting agents the active principles are mixed and ground with the carriers and the additives and can be diluted in this form.

Granulates such as covering granulates, impregnation granulates, homogeneous granulates and pellets usually contain 1 to 80% of the active principle. Thus, a 5% granulate can be composed, for example, of 5 parts of the active principle, 0.25 part of epichlorohydrin. 0.25 part of cetyl polyglycol ether, 3.50 parts of polyethylene glycol, and 91 parts of kaolin (preferred particle size 0.3 to 0.8 mm). The granulate can be prepared as follows:

The active substance is mixed with the epichlorohydrin and dissolved in 6 parts of acetone, after which the polyethylene glycol and the cetyl polyglycol ether are added. The solution thus obtained is sprayed onto kaolin and finally the acetone is evaporated off under vacuum. A microgranulate of this kind can be used advantageously for combatting soil fungi.

Liquid working forms

A general distinction is drawn between active principle concentrates that are dispersable or soluble in water and aerosols. Among the active principle concentrates that are dispersable in water there are, for example, wettable powders and pastes which as a rule contain 25–90% of the active principle in the commercially available packs and 0.01 to 15% of the active principle in the ready-for-use solutions. Emulsion concentrates contain 10 to 50% and solution concentrates 0.0001 to 20% of the active substance in the ready-for-use soluon. Thus, a 70% wettable powder consists, for example, of 70 parts of the active principle, 5 parts of sodium dibutylnaphthylsulfonate, and 3 parts of naphthalenesulfonic acids—phenolsulfonic acids—formaldehyde condensate (in the ratio of 3:2:1), 10 parts of kaolin, and 2 parts of chalk, e.g. Champagne chalk. A 40% wettable powder can, for example, consist of the following substances: 40 parts of the active principle, 5 parts of sodium ligninsulfonate, 1 part of sodium dibutylnaphtylsulfonate, and 54 parts of silica. A 25% wettable powder can be made in various ways. Thus, the latter can, for example, consist of 25 parts of the active substance, 4.5 parts of calcium ligninsulfonate, 1.9 parts of a mixture of chalk, such as Champagne chalk, and hydroxyethylethylenecellulose (1:1), 1.5 parts of sodium dibutylnaphthylsulfonate, 19.5 parts of silica, 19.5 parts of chalk, e.g. Champagne chalk, and 28.1 parts of kaolin. A 25% wettable powder can, for example, also consist of 25 parts of the active principle, 2.5 parts of isooctylphenoxypolyoxyethyleneethanol, 1.7 parts of a mixture of Champagne chalk and hydroxyethylcellulose (1:1), 8.3 parts of sodium silicate, 16.5 parts of kieselguhr, and 46 parts of kaolin. A 10% wettable powder can be made, for example, from 10 parts of the active principle, 3 parts of a mixture of sodium salts of saturated fatty alcohol sulfonates, 5 parts of naphthalenesulfonic acid/formaldehyde condensate, and 82 parts of kaolin. Other wettable powders can be mixtures of 5 to 30% of the active substance together with 5 parts of an absorbent carrier material such as silica, 55 to 80 parts of carrier material such as kaolin, and a dispersing agent consisting of 5 parts of sodium arylsulfonate and 5 parts of an alkylaryl polyglycol ether. A 25% emulsion concentrate can, for example, contain the following emulsifiable substances: 25 parts of the active principle, 2.5 parts of epoxidized vegetable oil, 10 parts of an alkylaryl sulfonate/fatty alcohol polyglycol ether mixture, 5 parts of dimethylformamide, and 57.5 parts of xylene.

Emulsions of the desired concentration which are particularly suitable for application to the leaves can be prepared from condensates of this type by dilution with water. In addition, other wettable powders can be prepared using different mixing ratios or other carrier materials and additives usual in formulation technology. The active principles are mixed thoroughly with the said additives in suitable mixers and ground using appropriate mills and rollers. Wettable powders of excellent wettability and buoyancy are obtained that can be diluted with water to give suspensions of the desired concentration and which are particularly suitable for application to the leaves. Such agents are also the object of the invention.

Preparations that have been formulated in the above-described manner, and which contain as the active component a compound of formula I (e.g. compound 1.4, 1.9, 1.14, 1.17, 2.9, 2.17, 2.24, 3.18, 4.3, 4.6, 4.8, 4.12, 4.15, or 4.23) can be used highly successfully for combatting phytopathogenic microorganisms. Other compounds from Tables 1 to 6 can also be used, with equally good or similar results.

Biological examples

The wettable mixtures used in the subsequent examples were formulated as described above.

EXAMPLE 2

Action against *Cercospora arachidicola* on peanut plants 3-week-old peanut plants were sprayed with a spray (0.02% of the active substance) prepared from a wettable powder of the active principle. After about 12 h the treated plants were dusted with a conidium suspension of the fungus. The infected plants were incubated for about 24 h at 90% relative humidity and then placed in a greenhouse at about 22° C. The incidence of the fungus infection was evaluated after 12 days.

In comparison with the untreated controls, plants that had been treated with the active principles of formula I displayed little or no fungal infestation.

Compounds 1.4, 1.9, 1.17, 2.17, 2.24, 2.9, 3.18, 4.12, 4.23, and 4.3 also inhibit the fungus infection in a concentration as low as 0.002%.

EXAMPLE 3

Action against *Puccinia graminis* on wheat (a) Residual protective action 6 days after sowing wheat plants were sprayed with a spray (0.06% of the active substance) prepared from wettable powder of the active principle. After 24 h the treated plants were infected with a uredospore suspension of the fungus. After incubation for 48 h at 95–100% relative humidity and about 20° C. the infected plants were placed in a greenhouse at about 22° C.

The development of the rust pustules was evaluated 12 days after the infection. Compounds of formula I displayed a strong action, as did compounds 1.4, 1.17, 2.17, 2.24, 4.3, and 4.8.

(b) Systemic action 5 days after sowing a spray solution made from wettable powder of the active principle (0.006% of the active substance referred to the soil volume) was poured over wheat plants. After 3 days the treated plants were infected with a uredospore suspension of the fungus. Following incubation for 48 h at 95–100% relative humidity and about 20° C. the infected plants were placed in a greenhouse at about 22° C. The development of the rust pustules was evaluated 12 days after the infection. Compounds of formula I exhibited a strong action. For example, compound 2.17 prevented entirely any spread of the disease.

EXAMPLE 4

Residual protective action against *Venturia inaequalis* on apple shoots

Apple saplings with fresh shoots 10 to 20 cm in length were sprayed with a spray (0.06% of the active substance) prepared from wettable powder of the active principle. After 24 h the treated plants were infected with a conidium suspension of the fungus. The plants were then incubated for 5 days at 90–100% relative humidity and kept for a further 10 days in a greenhouse at 20°–24° C. The scab formation was evaluated 15 days after the infection. Compounds 1.4, 1.9, 1.14, 1.17, 2.17, 3.18, and others inhibited the disease even in a concentration as low as 0.006%.

EXAMPLE 5

Residual protective action against *Podosphaera leucotricha* on apple shoots

Apple saplings with fresh shoots some 15 cm in length were sprayed with a spray (0.06% of the active substance) prepared from wettable powder of the active principle. After 24 h the treated plants were infected with a conidium suspension of the fungus and kept in an air-conditioned chamber at a relative humidity of 70% and a temperature of 20° C. The incidence of the fungal infection was evaluated 12 days later. Compounds of formula I displayed strong fungicidal action. Compounds 1.4, 1.9, 1.17, 2.9, 2.17, and 3.8, among others, inhibited the disease even in a concentration of 0.006%.

EXAMPLE 6

Action against *Erysiphe graminis* on barley (a) Residual protective action

Barley plants about 8 cm high were sprayed with a spray (0.02% of the active substance) prepared from wettable powder of the active principle. After 3-4 h the treated plants were dusted with conidia of the fungus. The infected barley plants were kept in a greenhouse at about 22° C. and the incidence of the fungus infestation was evaluated after 10 days.

(b) Systemic action

A spray (0.006% of the active substance referred to the soil volume) prepared from wettable powder of the active principle was poured over barley plants about 8 cm high. Care was taken that the spray mixture did not come into contact with the parts of the plant above ground level. After 48 h the treated plants were dusted with conidia of the fungus. The infected barley plants were kept in a greenhouse at about 22° C. and the incidence of the fungal infestation was evaluated after 10 days. In Experiments (a) and (b) the compounds of formula I displayed total action (fungal infection completely prevented). In Experiment (a) compounds 1.4, 1.9, 1.14, 1.17, 2.9, 2.17, 3.18, 4.3, 4.8, and 4.12 exhibited total action even at a dilution of 0.002%. Compounds 1.4, 1.9, and 2.17, inter alia, also exhibited this action in Experiment (b) at a concentration of 0.002%.

EXAMPLE 7

Action against *Botrytis cinerea* on beans

Residual protective action

Bean plants about 10 cm in height were sprayed with a spray (0.02% of the active substance) prepared from wettable powder of the active principle. After 48 h the treated plants were infected with a conidium suspension of the fungus. Following incubation of the infected plants for 3 days at 95-100% relative humidity and 21° C., the incidence of the fungal infestation was evaluated. The compunds of formula I inhibited the fungal infection totally. Compounds 1.14 and 2.9, for example, proved to be still fully effective at a concentration of 0.006% (zero incidence of the disease).

EXAMPLE 8

Action against *Plasmopara viticola* on vines

Residual preventive action

"Chasselas" vine saplings were treated in a greenhouse. At the 10-leaf stage 3 plants were sprayed with a spray (0.06% of the active substance) prepared from the active substance formulated as wettable powder. After the spray coating had dried, the plants were uniformly infected on the underside of the leaves with a spore suspension of the fungus. The plants were then kept in a moisture chamber for 8 days. After this period clear symptoms of disease were visible on the control plants. The number and size of the fungus colonies were used to evaluate the test products, and it was found that among others compounds 1.14 and 2.9 exhibited a very good action.

Compounds 1.4, 1.9, 1.14, 1.17, 2.9, 2.17, and 3.18, inter alia, inhibited the development of the fungus colonies almost entirely.

EXAMPLE 9

Action against *Fusarium nivale* on wheat

Wheat grains were contaminated with a spore suspension of the fungus and dried. The contaminated grains were steeped in a suspension of the test substance prepared from wettable powder (600 ppm of the active principle referred to the weight of the seeds). After two days the grains were laid out on suitable agar dishes and after a further four days the development of fungal colonies around the grains was evaluated. The number and size of the fungal colonies were used to evaluate the test products, and among other compounds 1.14 and 2.9 were found to have a very good action.

EXAMPLE 10

Action against *Helminthosporium gramineum*

Wheat grains were contaminated with a spore suspension of the fungus and dried. The contaminated grains were steeped in a suspension of the test substance prepared from wettable powder (600 ppm of the active principles referred to the weight of the seeds). After two days the grains were laid out on suitable agar dishes and after a further four days the development of fungal colonies was evaluated. The number and size of the fungal colonies were used to evaluate the test products.

Among others, compounds 1.4, 1.9, 1.14, 1.17, 2.9, and 2.17 inhibited the development of the fungus colonies almost totally.

EXAMPLE 11

Action against *Alternaria solani* on tomatoes

After 3 weeks of rearing tomato plants were sprayed with a spray (0.02% of the active substance) prepared from wettable powder of the active principle. After 24 h the plants were infected with a conidium suspension of the fungus. The fungicidal action was evaluated on the basis of the incidence of fungus infestation after incubation of the infected plants for 8 days at high relative humidity (95-100%) and at a temperature of 18°-22° C.

Compounds 2.17 and 2.24, among others, exhibited a very good action against Alternaria.

The results of the biological Examples 2-11 are proof of the exceptional activity and the broad action spectrum of the compounds against biologically very varied phytopathogenic fungi.

We claim:

1. A compound having the formula

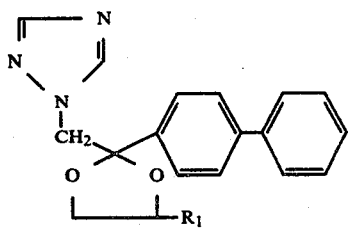

wherein $R_1$ represents hydrogen or a $C_1$–$C_3$ alkyl group, including their plant-compatible acid addition salts with organic and inorganic acids and their metal complex salts.

2. The compound of claim 1 wherein $R_1$ is $C_1$–$C_3$ alkyl.

3. The compound 1-[2-(4-diphenyl)-4-methyl-1,3-dioxolan-2-yl-methyl]-1H-triazole, including its acid addition salts and metal complexes.

4. The compound 1-[2-(4-diphenyl)-4-ethyl-1,3-dioxolan-2-yl-methyl]-1H-triazole, including its acid addition salts and metal complexes.

* * * * *